United States Patent
Buono

(10) Patent No.: US 8,774,911 B2
(45) Date of Patent: Jul. 8, 2014

(54) PEDICLE LOCATOR INSTRUMENT

(76) Inventor: Lee M. Buono, Marlton, NJ (US)

( * ) Notice: Subject to any disclaimer, the term of this patent is extended or adjusted under 35 U.S.C. 154(b) by 629 days.

(21) Appl. No.: 12/930,337

(22) Filed: Jan. 4, 2011

(65) Prior Publication Data

US 2012/0172937 A1     Jul. 5, 2012

(51) Int. Cl.
  *A61B 5/053* (2006.01)
  *A61B 5/00* (2006.01)

(52) U.S. Cl.
  CPC ......... *A61B 5/053* (2013.01); *A61B 2560/0462* (2013.01); *A61B 5/4566* (2013.01); *A61B 5/4887* (2013.01); *A61B 2560/0418* (2013.01)
  USPC .......................................... 600/547; 324/326

(58) Field of Classification Search
  USPC ........................................... 600/547; 324/326
  See application file for complete search history.

(56) References Cited

U.S. PATENT DOCUMENTS

| | | | |
|---|---|---|---|
| 6,215,293 B1 * | 4/2001 | Yim | 324/67 |
| 6,760,616 B2 * | 7/2004 | Hoey et al. | 600/547 |
| 6,844,713 B2 * | 1/2005 | Steber et al. | 324/67 |
| 7,050,848 B2 * | 5/2006 | Hoey et al. | 600/547 |
| 8,090,436 B2 * | 1/2012 | Hoey et al. | 600/547 |
| 2002/0072686 A1 * | 6/2002 | Hoey et al. | 600/547 |
| 2004/0181165 A1 * | 9/2004 | Hoey et al. | 600/547 |
| 2006/0224078 A1 * | 10/2006 | Hoey et al. | 600/546 |
| 2010/0049081 A1 * | 2/2010 | Hoey et al. | 600/547 |
| 2011/0313312 A1 * | 12/2011 | Hoey et al. | 600/547 |

* cited by examiner

*Primary Examiner* — Sean Doughtery
(74) *Attorney, Agent, or Firm* — Stuart M. Goldstein

(57) ABSTRACT

A manually operated pedicle locator instrument measures the static permittivity of matter to locate pedicles in vertebral or bony structures. The locator senses and compares the dielectric constants of the pedicle and the surrounding matter. When the operative component of the locator, the component which contains controlled capacitors, is placed over non-pedicle material, the locator will sense one dielectric constant. However, when it is placed over a pedicle, there is a different dielectric constant. The locator operates on this capacitance difference generated by differences in density. Circuitry in the locator senses this change and sends the change signal to indicator lights located on the locator. A switch on the locator allows the surgeon to select different levels of capacitance in order to identify thicknesses of different bony structures, i.e. structures in cervical, thoracic, and lumbar vertebral bodies.

7 Claims, 2 Drawing Sheets

PEDICLE LOCATOR INSTRUMENT

BACKGROUND OF THE INVENTION

Pedicle fixation is a common means to repair and attach vertebra relative to each other. It generally involves the insertion of a pedicle screw in two or more adjacent vertebral members and attaching a rod to each screw to eliminate movement between the members. The proper placement of pedicle screws in bony vertebral structures is critical in performing successful spine procedures. However, many surgeons are apprehensive when they must determine the proper placement of pedicle screws. Inaccurate placement greatly enhances the risk of screw malposition and other significant anatomical circumstances during surgery.

Image guidance is most commonly used to locate and identify the proper placement of pedicle screws. However, this process wastes valuable operative time and is done at great expense. It also increases patient risk of infection, pressure sores, blood loss, and the accompanying risks associated with general anesthesia. Prolonged exposure to fluoroscopic x-ray may also result in radiation burn and genetic mutation, resulting in malignancies.

There is thus a critical need for an instrument which will allow the surgeon to identify the correct entry point of a pedicle screw, thus obviating the need for image guidance and x-ray identification of the proper point of entry.

SUMMARY OF THE INVENTION

It is the object of the present invention to provide a manually operated pedicle locator instrument which is effective in efficiently and accurately locating pedicles in various types of bony vertebral structures in a non-invasive manner which is patient safe.

Specifically, the manually operated pedicle locator instrument of the present invention measures the static permittivity of matter to locate pedicles in vertebral or bony structures. The locator senses and compares the dielectric constants of the pedicle and the surrounding matter. When the operative component of the locator, the component which contains controlled capacitors, is placed over non-pedicle material, the locator will sense one dielectric constant. However, when it is placed over a pedicle, there is a different dielectric constant. The locator operates on this capacitance difference generated by differences in density. Circuitry in the locator senses this change and sends the change signal to indicator lights located on the locator. A switch on the locator allows the surgeon to select different levels of capacitance in order to identify thicknesses of different bony structures, i.e. structures in cervical, thoracic, and lumbar vertebral bodies.

The novel features which are considered as characteristic of the invention are set forth in particular in the appended claims. The invention, itself, however, both as to its design, construction and use, together with additional features and advantages thereof, are best understood upon review of the following detailed description with reference to the accompanying drawings.

DETAILED DESCRIPTION OF THE INVENTION

Figure 1:
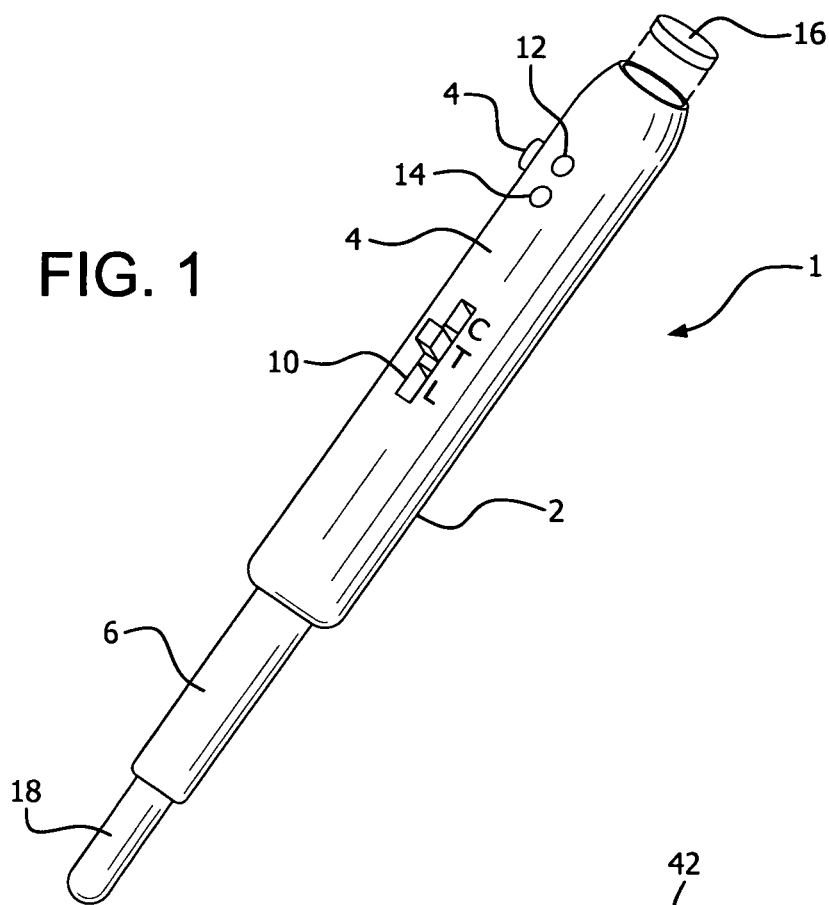
FIG. 1 is a front perspective view of the pedicle locator instrument of the present invention.
Figure 2:
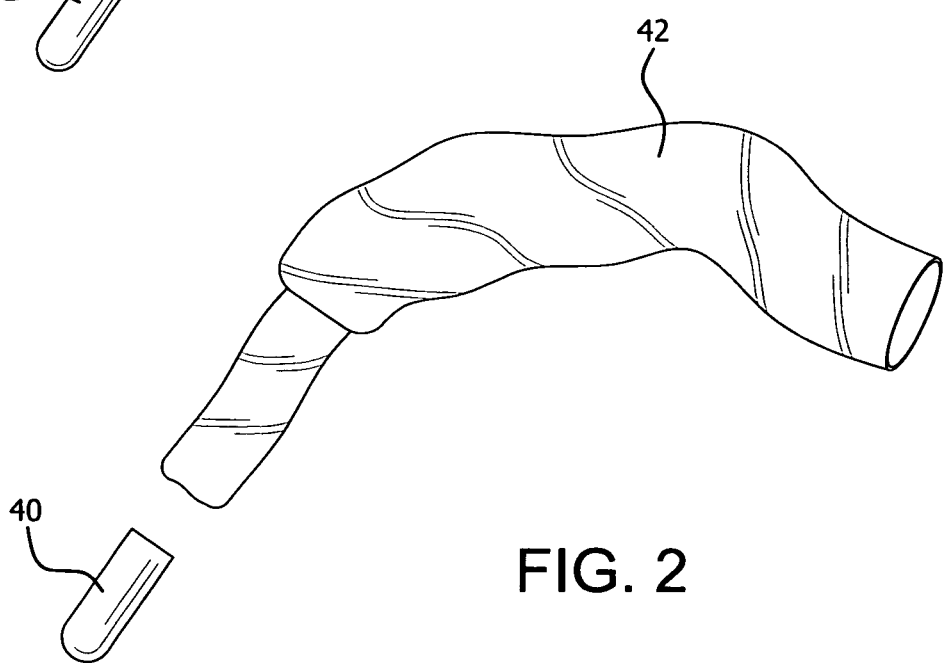
FIG. 2 is a view of the pedicle locator instrument's protective shroud.

Pedicle locator 1 is a unitary, self-contained instrument comprising elongated casing 2 with handle section 4 and pedicle detecting section 6. Handle section 4 comprises on/off switch 8, detection selection switch 10, LED indicator lights 12 (red) and 14 (green), and removeable casing cover 16 for the insertion of batteries 32 into casing 2. Detection selection switch 10 has three settings: C for cervical, T for thoracic, and L for lumbar.

Figure 3:
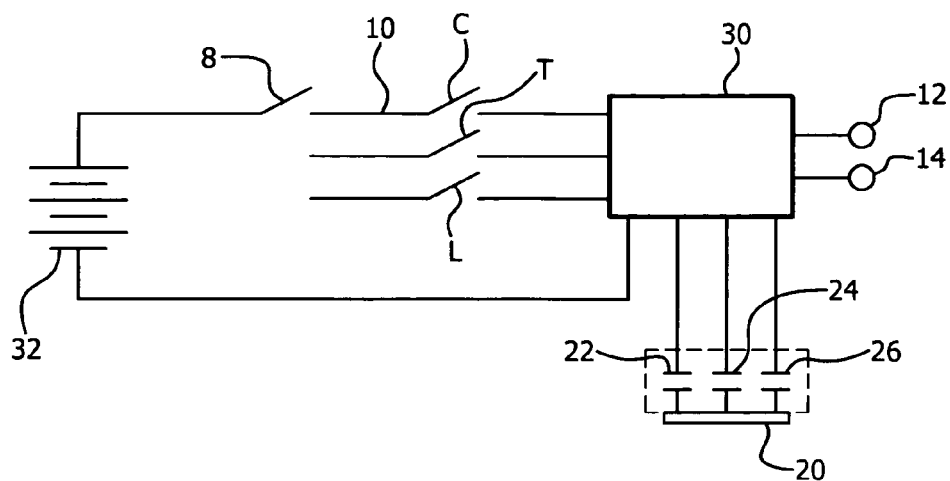
FIG. 3 is a simplified circuit schematic showing one embodiment of the present invention.
Figure 4:
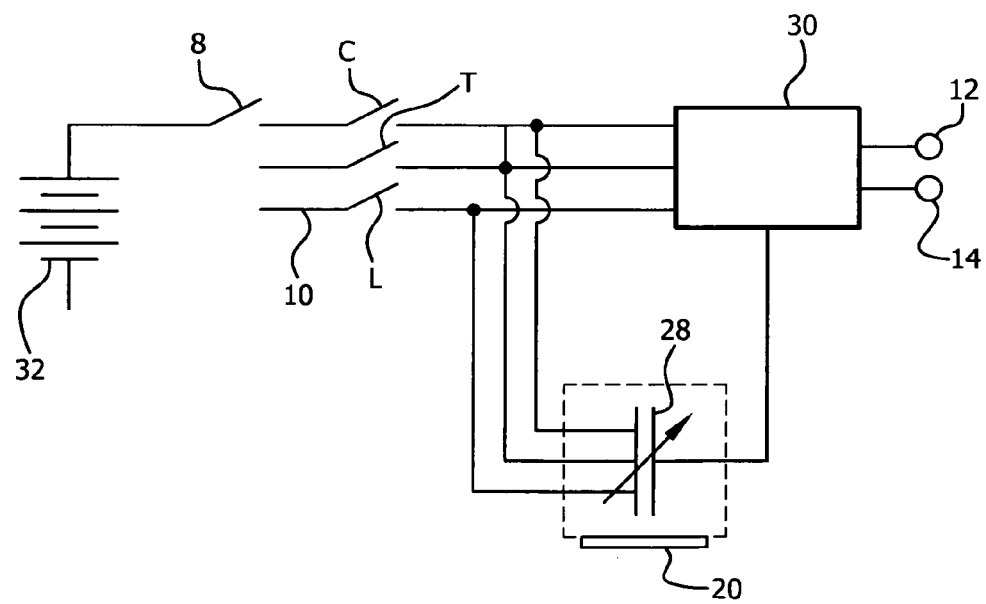
FIG. 4 is a simplified circuit schematic showing a second embodiment of the present invention.

Pedicle detecting section 6 comprises tip portion 18 which houses capacitor sensing component 20 and capacitors 22, 24 and 26 (FIGS. 3) and 28 (FIG. 4), which detect the change in capacitance of the capacitor sensing component. Pedicle detecting section 6 also houses circuit board 30 and the electronic circuitry which communicates the pedicle detecting section to on/off switch 8, detection selection switch 10, and indicator lights 12 and 14. The circuitry operates to provide the requisite signals to illuminate indicator. lights 12 and 14, upon the detection of a variation in capacitance of capacitor sensing component 20. In other words, sensing component 20 measures the static permittivity of pedicle material within bony vertebral structures by sensing the dielectric constant of the material and comparing it to the dielectric constant of surrounding material. The circuitry senses this capacitance differential and reports it to indicator lights 12 and 14.

The circuit technology utilized in pedicle locator instrument 1 is currently used in electronic wall stud finders and, in and of itself, forms no part of the herein invention. For example, reference is made to U.S. Pat. No. 6,844,713, which shows a wall stud finder device which utilizes electronic circuitry powered by removeable batteries, to detect wall studs as the device is run over the surface of the wall.

Pedicle locator instrument 1, however, is uniquely configured such that it can measure the more subtle, delicate variations in bony vertebral structures. In one embodiment of the invention, tip portion 18 encloses sensing component 20 and a plurality of capacitors 22, 24, and 26, each comprising capacitor plates having different gaps therebetween, such that they are calibrated to reflect different dielectric constants. These dielectric constants equate to the different thicknesses, i.e. static permittivity, of cervical (C), thoracic (T), and lumbar (L) bony vertebral structures. Detection selection switch 10 changes the baseline for the different dielectric constants of these structures, thereby setting which capacitor is to be utilized, depending on in which vertebral structure the pedicle is located.

In the second embodiment of the invention, tip portion 18 encloses sensing component 20 and single variable capacitor 28. Changing the setting of detection selection switch 10 changes the capacitance configuration of variable capacitor 28, which, depending on the setting, is calibrated to measure the static permittivity and corresponding dielectric constants of cervical, thoracic, and lumbar bony vertebral structures.

It is important that sterility be maintained throughout the pedicle screw insertion process. As a result, pliable tip member 40, made of plastic or rubber, is configured to cover tip portion 18 of locator 1. It will be disposed of after each use. Similarly, sterile protective shroud 42 is provided to encase handle section 4 and the upper portion of pedicle detecting section 6 of locator 1. Shroud 42 is made of a lightweight, but sturdy material, e.g. impregnated paper, and, like protective tip member 40, is disposable.

In operation, on/off switch 8 of locator 1 is turned on and the desired cervical (C), thoracic (T), or lumbar (L) setting is positioned on detection selection switch 10. Tip 18 and hence sensing component 20 is moved on and along the vertebral body in which the pedicle is located. Indicator light 12 will shine red, indicating constant capacitance of the baseline dielectric material. When tip 18 is moved over the pedicle, there is a change in material with a dielectric constant different from the surrounding baseline material. This will cause the capacitance of capacitors 22, 24, 26 or 28 to change, which, through circuit board 30, signals green indicator light 14 to illuminate, indicating the presence of the pedicle.

Certain novel features and components of this invention are disclosed in detail in order to make the invention clear in at least one form thereof. However, it is to be clearly understood that the invention as disclosed is not necessarily limited to the exact form and details as disclosed, since it is apparent that various modifications and changes may be made without departing from the spirit of the invention.

The invention claimed is:

1. A pedicle locator medical instrument for identifying pedicles and the presence and thicknesses of cervical, thoracic, and lumbar bony vertebral structures by measuring different dielectric constants of each of said bony vertebral structures, said instrument having an elongated length and comprising:

a casing having a given diameter and a lower and upper end, the casing extending the full elongated length of the medical instrument and comprising:

a manually operated handle section forming the upper end of the casing, the handle section containing circuit means for assisting in identifying pedicles within the vertebral structures, power means for providing electricity to the circuit means, and indicator means for providing notice of the presence of pedicles;

a pedicle locating section forming the lower end of the casing and having a smaller diameter than the upper end of the casing, said pedicle locating section comprising a singular tip section for movement over the different pedicles of the cervical, thoracic and lumbar bony vertebral structures, the singular tip section being the sole component of the medical instrument to measure the different dielectric constants of each of said bony vertebral structures;

capacitor means for measuring the different dielectric constants of said bony vertebral structures and the presence of the different pedicles and the different thicknesses of each of said bony vertebral structures, said capacitor means being located solely within the singular tip section and being electrically connected to the circuit means, the capacitor means calibrated for sensing the different pedicles and the different thicknesses of said bony vertebral structures and the presence of a cervical bony vertebral structure, the presence of a thoracic bony vertebral structure, and the presence of a lumbar bony vertebral structure, whereby placement of the singular tip section on a bony vertebral structure, results in changes in the capacitance within the capacitor means, indicating a cervical bony vertebral structure, a thoracic bony vertebral structure, or a lumbar bony vertebral structure, the indication of each of said bony vertebral structures being electronically transmitted to the indicator means; and switch means for altering the sensing of the capacitor means within the tip portion to alter the capacitance on the tip section to allow detection of the pedicles and the bony vertebral structures of different thicknesses.

2. The pedicle locator instrument as in claim 1 further comprising means for substantially enclosing the casing and for maintaining sterility of the instrument.

3. The pedicle locator instrument as in claim 2 wherein the means for substantially enclosing the casing comprises a protective shroud for covering the upper handle section and a portion of the pedicle locating section and a separate tip member to cover the singular tip section.

4. The pedicle locator instrument as in claim 1 wherein the capacitor means comprises multiple capacitors each detecting different capacitances.

5. The pedicle locator instrument as in claim 4 wherein the switch means controls the multiple capacitors which are utilized to indicate the presence of bony vertebral structures of different thicknesses.

6. The pedicle locator instrument as in claim 1 wherein the capacitor means comprises a variable capacitor.

7. The pedicle locator instrument as in claim 6 wherein the switch means changes the configuration of the variable capacitor to indicate the presence of vertebral structures of different thicknesses.

\* \* \* \* \*